(12) United States Patent
Shimizu et al.

(10) Patent No.: US 8,147,482 B2
(45) Date of Patent: Apr. 3, 2012

(54) ELECTRONIC CAPSULE FOR TREATING GASTROINTESTINAL DISEASE

(75) Inventors: Jeff Shimizu, Cortlandt Manor, NY (US); Karen I. Trovato, Putnam Valley, NY (US)

(73) Assignee: MEDIMETRICS Personalized Drug Delivery B.V., Eindhoven (NL)

( * ) Notice: Subject to any disclaimer, the term of this patent is extended or adjusted under 35 U.S.C. 154(b) by 0 days.

(21) Appl. No.: 12/305,118

(22) PCT Filed: Apr. 11, 2007

(86) PCT No.: PCT/IB2007/051307
§ 371 (c)(1),
(2), (4) Date: Dec. 16, 2008

(87) PCT Pub. No.: WO2007/148238
PCT Pub. Date: Dec. 27, 2007

(65) Prior Publication Data
US 2009/0275923 A1    Nov. 5, 2009

Related U.S. Application Data

(60) Provisional application No. 60/805,223, filed on Jun. 20, 2006.

(51) Int. Cl.
*A61K 9/22* (2006.01)
*A61K 9/48* (2006.01)
*A61M 31/00* (2006.01)
*A61B 5/05* (2006.01)

(52) U.S. Cl. ............ 604/891.1; 604/500; 604/503; 604/516; 604/424; 604/451; 604/452

(58) Field of Classification Search ........... 604/890.1, 604/891.1, 67; 600/118, 424, 348, 368; 424/452, 424/451
See application file for complete search history.

(56) References Cited

U.S. PATENT DOCUMENTS
4,543,955 A * 10/1985 Schroeppel ............... 600/348
(Continued)

FOREIGN PATENT DOCUMENTS
EP    1669026 A1    6/2006
(Continued)

OTHER PUBLICATIONS
U.S. Appl. No. 60/644,540, filed Jan. 18, 2005.
(Continued)

*Primary Examiner* — Jackie Ho
*Assistant Examiner* — Bradley Thomas, Jr.
(74) *Attorney, Agent, or Firm* — Stephen B. Salai, Esq.; Michael J. Didas, Esq.; Harter Secrest & Emery LLP

(57) ABSTRACT

The present invention discloses an ingestible capsule containing drug and a method for controlled administration of the drug in a mammal for treatment of a disease of the GI tract. The capsule has electronic control means for dispensing the drug substantially to the diseased tissue sites of the GI tract, according to a pre-determined drug release profile obtained prior to administration from the specific mammal.

22 Claims, 1 Drawing Sheet

U.S. PATENT DOCUMENTS

| | | | |
|---|---|---|---|
| 5,109,850 A * | 5/1992 | Blanco et al. | 600/368 |
| 5,279,607 A | 1/1994 | Schentag et al. | |
| 5,318,557 A * | 6/1994 | Gross | 604/891.1 |
| 5,558,640 A * | 9/1996 | Pfeiler et al. | 604/67 |
| 5,728,396 A * | 3/1998 | Peery et al. | 424/422 |
| 5,797,898 A | 8/1998 | Santini, Jr. et al. | |
| 6,632,216 B2 | 10/2003 | Houzego et al. | |
| 6,884,239 B2 | 4/2005 | Houzego et al. | |
| 6,929,636 B1 | 8/2005 | Von Alten | |
| 6,950,690 B1 | 9/2005 | Meron et al. | |
| 2002/0183721 A1 * | 12/2002 | Santini et al. | 604/890.1 |
| 2003/0213495 A1 | 11/2003 | Fujita et al. | |
| 2004/0087839 A1 | 5/2004 | Raymond et al. | |
| 2004/0122315 A1 | 6/2004 | Krill | |
| 2004/0162501 A1 | 8/2004 | Imran | |
| 2004/0242962 A1 * | 12/2004 | Uchiyama | 600/118 |
| 2005/0058701 A1 | 3/2005 | Gross et al. | |
| 2005/0283048 A1 * | 12/2005 | Gill et al. | 600/121 |

FOREIGN PATENT DOCUMENTS

| | | |
|---|---|---|
| WO | 9205822 A1 | 4/1992 |
| WO | 2005105053 A2 | 11/2005 |
| WO | 2006056944 A1 | 6/2006 |
| WO | 2006064502 A2 | 6/2006 |

OTHER PUBLICATIONS

U.S. Appl. No. 60/644,539, filed Jan. 18, 2005.
U.S. Appl. No. 60/644,538, filed Jan. 18, 2005.
U.S. Appl. No. 60/644,518, filed Jan. 18, 2005.
U.S. Appl. No. 60/606,276, filed Sep. 1, 2004.
U.S. Appl. No. 60/605,364, filed Aug. 27, 2004.
U.S. Appl. No. 60/738,238, filed Nov. 18, 2005.
Johannessen E.A. et al., "An ingestible electronic pill for real time analytical measurements of the gastrointestinal tract", Google Scholar.
Nugent, S.G. et al., "Intestinal luminal pH in inflammatory bowel disease: possible determinants and implications for therapy with aminosalicylates and other drugs", Gut, 2001, pp. 571-577, vol. 48.

* cited by examiner

ELECTRONIC CAPSULE FOR TREATING GASTROINTESTINAL DISEASE

RELATED REFERENCES

The present disclosure is related to U.S. Provisional Patent Application No. 60/644,540, entitled "Electronicially Controlled Capsule For Releasing Radiation", and filed Jan. 18, 2005, U.S. Provisional Patent Application No. 60/644,539, entitled "Electronicially Controlled Capsule", and filed Jan. 18, 2005, U.S. Provisional Patent Application No. 60/644, 538, entitled "Electronicially Controlled Ingestible Capsule", and filed Jan. 18, 2005, U.S. Provisional Patent Application No. 60/644,518, entitled "System And Method For Controlling Traversal Of An Ingested Capsule", and filed Jan. 18, 2005, U.S. Provisional Patent Application No. 60/606,276, entitled "Electronically Controlled Pill And System For Delivering At Least One Medicament", and filed Sep. 1, 2004, U.S. Provisional Patent Application No. 60/605,364, entitled "Electronically And Remotely Controlled Pill And System For Delivering At Least One Medicament", and filed Aug. 27, 2004, and U.S. Provisional Patent Application No. 60/738,238, entitled "System and Method for Interacting With a Cell or Tissue", and filed Nov. 18, 2005, with each of the foregoing references being assigned to the Assignee of the present disclosure and hereby being expressly incorporated by reference as part hereof.

The invention relates to an ingestible electronic pill or capsule and method for administering a drug for the treatment of a disease in the gastrointestinal tract of a mammal according to a pre-determined drug release profile, the gastrointestinal tract having sites of diseased tissue and normal tissue. The capsule comprises a drug reservoir; drug dispensing means; electronic control circuitry means for controlling the dispensing means, including memory means for storage of data specific to the pre-determined drug release profile for the mammal (i.e., human being or animal); and an outer protective shell housing the capsule contents, wherein the drug is dispensed substantially at the diseased sites.

Inflammatory bowel diseases (IBD) include Crohn's Disease (CD) and Ulcerative Colitis (UC). Both are chronic autoimmune diseases, which are expensive to treat. During periods of active disease the intestinal mucosa are subject to inflammation, bleeding, and ulcerations. Active disease is induced into remission by drug therapies. Between periods when the disease is active, drug therapies are used to maintain remission and hopefully allow for mucosal healing. The first line therapy is aminosalicylates (5-ASA), which are non-steroidal anti-inflammatory drugs (NSAIDs). These medications are taken daily, often several times daily. The action appears to be topical and thus the drug formulations aim to deliver 5-ASA at the site of disease. Crohn's disease typically occurs at the ileum, ascending colon, or both, however it can occur anywhere along the GI tract. Diseased tissue may occur in local regions or sites separated by healthy or normal tissue, commonly called 'skip lesions'.

Ulcerative Colitis starts at the rectum and develops farther up as the disease progresses. For disease near the rectum up to the sigmoid colon, enemas, suppositories, or foams are common formulations. Delayed release pills, or azo-splitting pro-drugs have been formulated to target delivery to the colon. Corticosteroids (prednisone, prednisolone) are commonly given to treat active flare-ups. There are many side effects to long-term steroid use, so the aim is to withdraw this therapy quickly. A more recent advancement in corticosteroid therapy is the application of budesonide. Budesonide has a high topical corticosteroid activity and a substantial first pass elimination. The high metabolism reduces the instance of side effects from long-term use. For patients who do not respond well to the above treatments, use of biologic therapy has emerged as a critical treatment. Remicade (infliximab) is an approved therapy for Crohn's Disease and recently (September 2005) received approval for ulcerative colitis. Remicade is an antibody therapy aimed at blocking TNF-alpha, an important cytokine in the inflammatory response. Remicade is an expensive treatment (about $1500 per application) given by injection every two to six weeks. Remicade also can have serious side effects, and thus is a treatment of last resort. However for patients with moderate to severe disease who do not respond to milder treatments, Remicade has proven to be very effective.

To overcome some of the disadvantages resulting from the administration of such oral and injectable medications and anally introduced medications including enemas, suppositories and foams for treating IBD, various devices, apparatus and methods for drug delivery have been more recently disclosed. Houzego et. al. (U.S. Pat. No. 6,632,216) and Schentag et. al. (U.S. Pat. No. 5,279,607) both describe a means of tracking the location of a pill and releasing a burst of medication upon application of an external RF field. The location of the pill is tracked as it passes the patient's gastrointestinal (GI) tract. When it reaches a desired location, a user triggers the release of the drug. The pill expels the entire contents of a drug reservoir in a short amount of time (burst release). However, these methods would not be useful for GI tract diseases such as IBD which may require drug dispensing of various amounts of drug with time at several disease sites within the GI tract. Various mechanisms for drug release have been explored and described.

Santini Jr. et al. (U.S. Pat. No. 5,797,898) described "Microchip drug delivery devices" which control both the rate and time of release of multiple chemical substances by a pre-programmed microprocessor, remote control, or by biosensors. Drugs are stored in an array of reservoirs on a substrate and sealed by caps before being released. The most attractive application is implanted drug release of small quantities at relatively long intervals.

Other patents and publications disclosing ingestible capsules or devices for taking data readings or dispensing medications within the gastrointestinal tract include U.S. Pat. Nos. 5,318,557; 6,884,239; 6,929,636; and 6,950,690; U.S. patent application No. 20030213495 published on Nov. 20, 2003; No. 20040087839 published on May 6, 2004; No. 20040162501 published on Aug. 19, 2004; and No. 20050058701 published on Mar. 17, 2005; and PCT Publication Number WO 92/05822 published on Apr. 16, 1992. Also, an article downloaded from the Google Scholar website entitled "An Ingestible Electronic Pill for Real Time Analytical Measurements of the Gastrointestinal Tract" by E. A. Johannessen et al discloses an ingestible, noninvasive pill device containing various analytical Microsystems for measuring parameters in the Gastrointestinal (GI) tract.

Additional patent applications disclosing ingestible capsules, the contents of which are hereby incorporated by reference are the following U.S. patent applications: U.S. Patent Application entitled "*Electronically Controlled Ingestible Capsule For Sampling Fluids In Alimentary Tract*"—Karen Trovato and Judy Naamat. U.S. Ser. No. 050030, Filed Jan. 18, 2005; U.S. Patent Application entitled "Electronically Controlled Capsule"—Karen Trovato and Judy Naamat. U.S. Ser. No. 050028, Filed Jan. 18, 2005; U.S. Patent Application entitled "*Electronically Controlled Capsule For Releasing Radiation*"—Karen Trovato. U.S. Ser. No. 050027, Filed Jan. 18, 2005; U.S. Patent Application entitled "System and Method for Controlling Traversal of an Ingested Capsule"—Karen Trovato, Martin Ouwerkerk, Daniel Herzka and Judy Naamat. U.S. Ser. No. 050029, Filed Jan. 18, 2005; U.S. Patent Application entitled "*Electronically And Remotely Controlled Pill And System For Delivering At Least One Medicament*" K. Trovato and G. Spekowius, U.S. Ser. No. 040321, Filed Aug. 27, 2004; and U.S. Patent Application entitled "*Electronically Controlled Pill And System For Delivering At Least One Medicament*" K. Trovato U.S. Ser. No. 040322, Filed Sep. 1, 2004.

However, problems still persist with these systems and methods for treating GI tract diseases, especially Inflammatory Bowel Disease (IBD), which includes Crohn's Disease and Ulcerative Colitis, which the herein disclosed methodology and systems overcome.

According to this invention, an ingestible capsule or pill containing a drug therein is disclosed which can be ingested by a mammal (i.e., human being or animal) into the GI tract for controlled dispensing of the drug substantially at the diseased tissue sites, according to a pre-programmed and pre-determined drug release profile over time.

Specifically, it is an object of this invention to provide an ingestible capsule for administering a drug for the treatment of a disease in the gastrointestinal tract of a mammal according to a pre-determined drug release profile, the gastrointestinal tract having sites of diseased tissue and normal tissue, the capsule comprising:

a drug reservoir for storing the drug;

drug dispensing means for dispensing or stopping the dispensing of the drug from the drug reservoir into the gastrointestinal tract;

electronic control circuitry means communicating with the drug dispensing means for regulating the amount and time interval for dispensing of the drug into the gastrointestinal tract by the drug dispensing means according to the predetermined drug release profile, wherein the electronic control circuitry means further comprises memory means for storage or updating of data specific to the pre-determined drug release profile for the mammal; and a non-digestible outer protective shell housing the drug reservoir, drug dispensing means and electronic control circuitry means; wherein the drug is substantially dispensed at the diseased tissue sites.

Another object is to provide a capsule further comprising sensor means within the capsule for sensing one or more biological conditions in the gastrointestinal tract; wherein the sensor means communicates with the electronic control circuitry means for activating the control circuitry means to dispense drug according to the drug release profile, or to determine or modify the drug release profile.

Another object is to provide a capsule wherein the biological condition sensed by the sensor means is selected from the group consisting of pH level, presence or absence of bacteria or enzymes, and the presence or absence of blood.

Another object is to provide a capsule further comprising a wireless communication means for transmitting and/or receiving signals to and from a second communications means located exterior to the body of the mammal; wherein upon receiving a signal from the second communications means, the wireless communication means communicates with the electronic control circuitry means to activate the control circuitry means to dispense drug according to the drug release profile.

Another object is to provide a capsule wherein the disease is selected from the group consisting of inflammatory bowel disease, celiac disease and intestinal cancer.

Another object is to provide a capsule wherein the disease is Crohn's Disease or Ulcerative Colitis and the drug is selected from the group consisting of aminosalicylates (e.g., 5-aminosalicylates, sulfasalazine, mesalamine, olsalazine, balsalazide), corticosteroids (e.g., prednisone, budesonide), biologics (e.g., infliximab), anti-coagulant drugs, immunomodulators (e.g., 6-MP, azathioprine, methotrexate), probiotics and antibiotics (e.g., metronidazole, ciprofloxacin).

Another object is to provide a method for administration of a drug for the treatment of a disease in the gastrointestinal tract of a mammal according to a pre-determined drug release profile, the gastrointestinal tract having sites of diseased tissue and normal tissue, the method comprising:

orally administering to the mammal an ingestible capsule that includes the drug;

dispensing the drug in the gastrointestinal tract according to a predetermined drug release profile, wherein the drug is substantially dispensed at the diseased tissue sites;

wherein the capsule comprises:

a drug reservoir for storing the drug;

drug dispensing means for dispensing or stopping the dispensing of the drug from the drug reservoir into the gastrointestinal tract;

electronic control circuitry means communicating with the drug dispensing means for regulating the amount and time interval for dispensing of the drug into the gastrointestinal tract by the drug dispensing means according to the predetermined drug release profile, wherein the electronic control circuitry means further comprises memory means for storage or updating of data specific to the pre-determined drug release profile for the mammal;

and a non-digestible outer protective shell housing the drug reservoir, drug dispensing means and electronic control circuitry means.

Another object is to provide a method wherein the capsule further comprises sensor means within the capsule for sensing one or more biological conditions in the gastrointestinal tract; wherein the sensor means communicates with the electronic control circuitry means for activating the control circuitry means to dispense drug according to the drug release profile, or to determine or modify the drug release profile.

Another object is to provide a method wherein the biological condition sensed by the sensor means is selected from the group consisting of pH level, presence or absence of bacteria or enzymes, and the presence or absence of blood.

Another object is to provide a method further comprising a wireless communication means for transmitting and/or receiving signals to and from a second communications means located exterior to the body of the mammal; wherein upon receiving a signal from the second communications means, the wireless communication means communicates with the electronic control circuitry means to activate the control circuitry means to dispense drug according to the drug release profile.

Another object is to provide a method wherein the disease is selected from the group consisting of inflammatory bowel disease, celiac disease and intestinal cancer.

Another object is to provide a method wherein the disease is Crohn's Disease or Ulcerative Colitis and the drug is selected from the group consisting of aminosalicylates (e.g., 5-aminosalicylates, sulfasalazine, mesalamine, olsalazine, balsalazide), corticosteroids (e.g., prednisone, budesonide), biologics (e.g., infliximab), anti-coagulant drugs, immunomodulators (e.g., 6-MP, azathioprine, methotrexate), probiotics and antibiotics (e.g., metronidazole, ciprofloxacin).

These and other aspects of the invention are explained in more detail with reference to the following embodiments and with reference to the figures.

Figure 1:
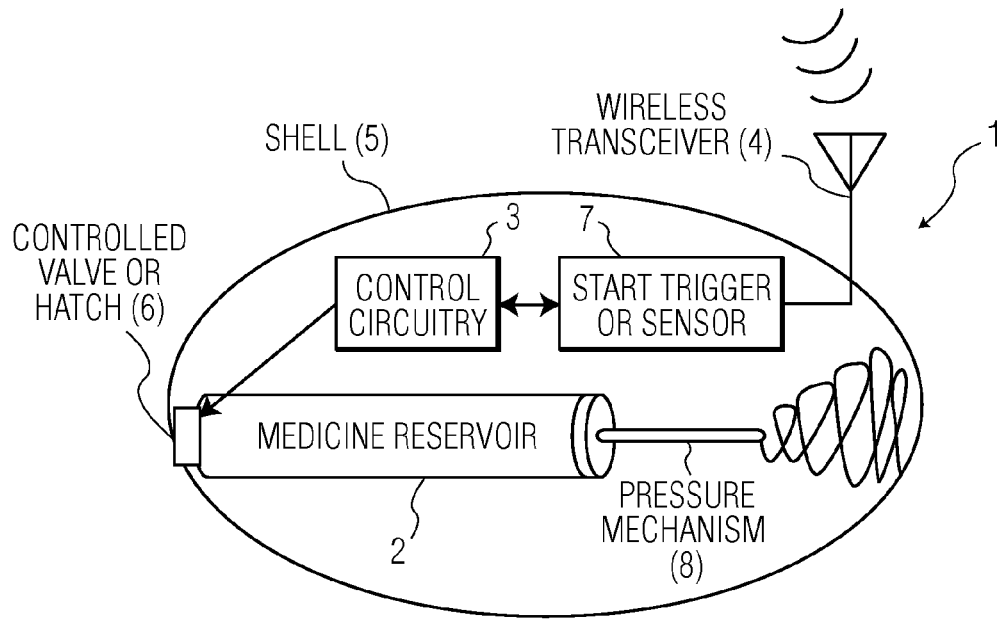
FIG. 1 is a conceptual representation of an ingestible capsule according to the invention.

Existing medications for the treatment of IBD have a several disadvantages. The 5-ASA drugs act topically. Thus various drug delivery strategies are employed to target the medication to the location of interest. Mesalamine comes in delayed release or controlled release formulations employing enteric coatings and microspheres. These forms delay the release of the drug to target the terminal ileum and/or the colon. Osalazine and balsalazide are prodrug formations that are cleaved in the colon by the action of colonic bacteria, azoreductase. After reaction in the colon the active form of the drug is delivered to the targeted site, generally the descending colon. Drug targeting based on these conventional formulation strategies has the disadvantage of poor precision. The release is based on statistical averages and the availability profile is difficult to control. Different chemistries or formulations must be developed to target different regions. For example, a formulation targeting the descending colon for UC, is poorly matched to the treatment of CD where the patient has involvement in the ileum. Furthermore, the location of disease is variable both between patients and within a given patient over time.

Other strategies for targeting the descending colon and rectum for UC include the use of suppositories, foams, and enemas. These bring the obvious disadvantages of patient discomfort, acceptance, and time required for treatment. Oral medications are always preferred when available and effective.

According to the invention herein, an electronic capsule or pill is ingested and travels naturally through the patient's gastrointestinal (GI) tract. The pill contains a medication or drug reservoir that is dispensed under electronic control. The capabilities allow precise delivery at a specific location, a complex release profile, delivery controlled by external signal, or delivery controlled by on board sensors. Precisely controlled topical application of medication at the site of disease is a unique benefit of such a device and method of administration.

Furthermore, the electronic pill can provide an effective oral delivery vehicle for the application of antibody treatments. Infliximab (Remicade) is an effective treatment that must be delivered by intravenous injection. This bears heavy convenience and cost penalties. Relatively high doses must be administered to reach therapeutic plasma concentrations. Additionally the drug is in systematic circulation for several weeks, raising the chances for side effects and other complications.

Also, the present invention discloses the use of an electronic capsule or pill for the topical treatment of GI disease, particularly IBD. The electronic pill contains a drug reservoir. The drug is dispensed under electronic control allowing the creation of complex and precise release profiles. Delivery of the drug and determination of the release profile is based on knowledge of or captured data from the individual patient. The pill is taken orally. Knowledge of the patient is used to precisely target locations in the patient's GI tract where the disease is present.

According to the invention, an ingestible capsule and method are disclosed for the treatment of gastro-intestinal disease. The preferred embodiment is a pill for the topical application of a drug in the treatment of inflammatory bowel disease. The drug release profile may be tailored to the needs of the individual patient. That is, since the location of IBD can vary, the effect of the invention is to deliver the medication primarily only where the disease is present for a given individual.

FIG. 1 shows a conceptual representation of the electronic pill or capsule 1. The pill contains a drug reservoir 2 containing medication. Dispensing of the medication is regulated by electronic control circuitry 3 of the pill. The control circuitry also has memory where data specific to the desired release profile may be updated and stored. The pill may optionally have a wireless transceiver 4 for communication with an external communications means for sending and receiving signals, before or during the time it is in the patient. All of the pill components are contained in an outer shell 5 that protects the pill components from the body environment of the patient, and vice versa. Drug dispensing means, such as a controlled valve or hatch 6 is provided. The pill may also optionally have one or more sensors 7 for sensing biological conditions in the GI tract for communicating the same to the control means 3 to activate drug dispensing according to the pre-programmed, pre-determined drug release profile for a specific patient. A pressure mechanism 8 that provides the necessary pressure or force to cause the drug to be dispensed by the dispensing means in a controlled way according to the drug profile. Energy or pressure from the pressure mechanism 8 can be mechanical, like a motor or a spring, chemical, from a reaction creating a gas or the intake of water in an osmotic engine, a micro-dispensing pump, like a piezoelectric chamber system or MEMs micropump. A valve is possible but not necessary in all embodiments. Additionally, power or battery means (not shown) powers the control means 3 in order for each of the electromechanical components to operate during the drug dispensing time period.

Figure 2:
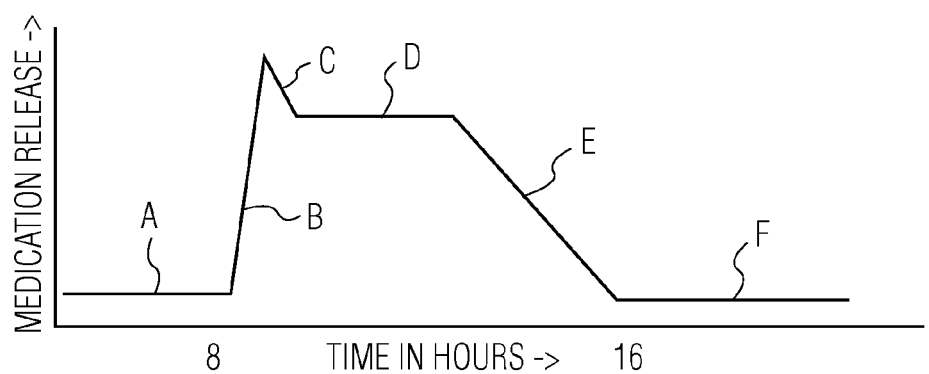
FIG. 2 is a chart illustrating an exemplary pre-determined, pre-programmed drug dispensing timing pattern for the ingestible capsule in accordance with the present invention.

As shown by the exemplary preset dispensing timing pattern illustrated by FIG. 2, at dispensing time periods A, D and F, identical quantities of the medicament are dispensed throughout each of these dispensing time periods. Therefore, during these dispensing time periods, the valve 6 is kept open by the control circuitry 3 to provide a fixed valve opening (or frequency of opening) for dispensing a predictable quantity of the medicament at each moment in time of dispensing time periods A, D and F. Approximately the same amount of medicament is dispensed at each moment in time during dispensing time periods A and F. During dispensing time period D, a higher quantity of medicament is dispensed than during dispensing time periods A and F.

However, at dispensing time periods B, C and E, as shown by FIG. 2, different quantities of the medicament are dispensed at each moment in time. Therefore, during dispensing time periods B, C and E, the valve opening is varied accordingly by the electronic control circuitry 3 to dispense a quantity of the medicament varying at each moment in time. During dispensing time period B, the quantity of medicament dispensed during each moment in time is increased compared to the previous moment in time; whereas during dispensing time periods C and E, the quantity of medicament dispensed during each moment in time is decreased compared to the previous moment in time.

The capsule is non-digestible and passes through the digestive or GI tract of the mammal without alteration and protects the contents housed therein while in the GI tract. The outer protective shell can be coated or made of those materials well known to one of ordinary skill in the art, such as inert materials like inert plastics (e.g., polycarbonate), Teflon or a ceramic.

In one embodiment, data from a previous patient examination is used to determine the release profile. Patients with IBD often undergo endoscopy to diagnose the patient or examine the progression of disease. Images from endoscopy show the location where disease is active. This data may then be used to program the pill to dispense in a pattern matching the involvement area. Location of involvement may be translated into time based on statistical norms of intestinal motility. The drug is topically acting, such as 5-ASA or budesonide. At the doctor's office or pharmacy the desired profile is downloaded to the pill. If this level of customization proves logistically difficult in the early stages, then pills of a limited number of average release profiles can be created by the pharmaceutical manufacturer and selected or prescribed by the doctor. The patient then swallows the pill. Retention time in the stomach is often the greatest variable in GI transit time. In the preferred embodiments, the pill contains a pH sensor. The sensor may be a simplified arrangement that needs only report when pH rises above a threshold (e.g. pH >3.0) indicating passage out of the stomach. This event then starts a timer. The release profile is programmed as rate of administration of drug versus time. With an electronic pill the profile can be complex. For example, a patient with CD may have multiple areas of involvement separated by healthy tissue, called skip lesions. The programmed release may then include starts and stops. It may also dispense more medication in areas where disease is more active. With IBD, many of the medications are taken daily, or more often. Over the course of time, the release profiles may be altered depending on the response of the patients. For example, the area of application may be expanded, or drug concentrations increased if the patient's conditions worsen. Similarly the amount of medication or coverage area can decrease as the patient improves.

In order to better define the location of the pill, additional sensors may be employed. For example, a continuous pH sensor would give further information. The pH of the GI tract steadily increases, about 5.0-6.5 in the jejunum, to 6.0-7.5 in the ileum, and 6.0-8.0 in the colon. A continuous sensor, or a series of discrete threshold sensors would provide more certainty of location as the pill progresses. Another valuable sensor would be that for bacteria or enzymes. There is a rather abrupt and dramatic increase in the bacterial density and variety after the ileocecal junction. For example a threshold sensor for azoreductase would indicate when the pill passes into the colon.

In another embodiment, the pill contains a wireless communication link. The pill for example may transmit a beacon signal. Triangulation of the signal allows determination of position. When the pill reaches a desired or critical position, a control signal is sent from outside the body to the pill in order to begin dispensing or execution of the programmed release profile.

In yet another embodiment dispensing of the drug is determined largely by measurements taken on the pill. For example, the pill may include a sensor for the presence of blood. In IBD, active disease is characterized by ulcerations. Location of blood in the intestines indicates presence of disease and a target for dispensing of the medication. The medication may be normally administered drugs such as 5-ASA or corticosteroids. An alternative is to administer a coagulating drug to reduce bleeding directly, and its associated effects. By location of the site of bleeding, we can apply the coagulating drug in a higher concentration, thus achieving better results.

In the above examples we consider the dispensing of topical medications such as 5-ASA and budesonide. The electronic pill delivery platform also presents an opportunity to deliver biologic drugs topically. For example, infliximab (Remicade) is an effective treatment for more severe cases of IBD. This is an antibody-based drug delivered by intravenous injection. After entering systematic circulation, the drug is made available to diseased tissue in the GI tract. Biologic drugs are often poor candidates for oral delivery since they are degraded rapidly in the stomach and upper small intestines, and may be poorly absorbed through the gut wall. The electronic pill provides an excellent means for protection of the drug in a reservoir until the desired site is reached. In the case of IBD, the inflamed or diseased tissue is accessible to the gut lumen. Dispensing of the biologic at the site of inflammation would make it readily available to the diseased tissue. In this manner the diseased tissue may be directly targeted, and the concentration in systematic circulation could be dramatically decreased thus reducing potential side effects.

Typical drugs that can be used according to the method of the invention, but not limited thereto, are herein discussed. Aminosalicylates are compounds that contain 5-aminosalicylic acid (5-ASA). These drugs, which can be given either orally or rectally, interfere with the body's ability to control inflammation. Corticosteroids are fast-acting anti-inflammatory drugs. In pill form these include: prednisone, methylprednisolone, hydrocortisone. One of the latest oral corticosteroids is budesonide. Representing a new class of corticosteroids called nonsystemic steroids, it targets the intestine rather than the whole body. As their name implies, immunomodulators weaken or modulate the activity of the immune system. Immunomodulators used in IBD are azathioprine and 6-mercaptopurine. Other immunomodulators to treat IBD are cyclosporine A and tacrolimus. Methotrexate is given by weekly injections.

Although there are several antibiotics that may be effective for certain people, the two most commonly prescribed in IBD are: Metronidazole, and Ciprofloxacin. Biologics interfere with the body's inflammatory response in IBD by targeting specific molecular players in the process such as cytokines. Infliximab is the first FDA-approved biologic therapy for Crohn's disease, and was recently approved for ulcerative colitis. Additional biologic therapies under investigation for IBD include two other antibodies to TNF, adalimumab and CDP-870. Drugs targeting a number of other cytokines and the inflammatory response, such as alpha 4 integrin, interleukin-6, interleukin-12, interferon gamma, and GM-CSF, are being evaluated in clinical trials.

In another embodiment, there is evidence that the luminal pH of the intestines is lowered when inflammatory bowel disease is active. Normally pH gradually rises as it travels through the intestines with a small drop at the transition from small to large intestines. However patients with inflammatory bowel disease tend to show lower pH values. Data is limited and thus a complete picture is not available. Therefore it would follow that when disease is active and tissue is inflamed, the inflammatory response lowers pH compared to 'normal'. Thus local measurement of an abnormally low pH indicates that disease is present in that spot. Thus, according to the invention drug medication would be dispensed there. When pH returns to normal, dispensing of drug can be discontinued. Further, the larger the deviation from normal, the more active the disease is and the greater the need for dispensing more drug at that location. So the rate of dispensing is proportional to the amount the luminal pH differs from normal. A reference article on pH is, S. G. Nugent et. al., "Intestinal luminal pH in inflammatory bowel disease: possible determinants and implications for therapy with aminosalicylates and other drugs", Gut, Vol. 48, pp. 571-577 (2001).

The preferred application, as described, is for the treatment of IBD. The above means also may similarly be applied in the treatment of other GI diseases where local topical delivery provides benefits. For example, treatment of GI tumors or treatment of celiac disease may be effectively targeted.

This invention will provide a means and method for the treatment of localized diseases of the gastro-intestinal system, by local and targeted application of medication, which is individualized for each specific patient having a specific disease condition in the GI tract.

While the present invention has been described with respect to specific embodiments thereof, it will be recognized by those of ordinary skill in the art that many modifications, enhancements, and/or changes can be achieved without departing from the spirit and scope of the invention. Therefore, it is manifestly intended that the invention be limited only by the scope of the claims and equivalents thereof.

The invention claimed is:

1. An ingestible capsule for administering a drug for treatment of a disease in a gastrointestinal tract of a mammal according to a pre-determined drug release profile, the gastrointestinal tract having sites of diseased tissue and normal tissue, the capsule comprising:
   a drug reservoir for storing the drug;
   a drug dispensing device for dispensing or stopping the dispensing of the drug from the drug reservoir into the gastrointestinal tract;
   an electronic control circuitry communicating with the drug dispensing device for regulating amount and time interval for dispensing of the drug into the gastrointestinal tract by the drug dispensing device according to a predetermined drug release profile, wherein the electronic control circuitry further comprises a memory for storage or updating of data specific to the predetermined drug release profile for the mammal;
   at least one sensor configured to communicate with the electronic control circuitry; and
   a non-digestible outer protective shell housing the drug reservoir, the drug dispensing device and the electronic control circuitry; wherein the drug is substantially dispensed at the diseased tissue sites by the electronic control circuitry activating the drug dispensing device in response to detection of a biological condition by the at least one sensor,
   wherein the at least one sensor is a threshold sensor that detects a level of the biological condition crossing a predetermined threshold, and
   wherein the electronic control circuitry is configured to start a timer for the dispensing of the drug into the gastrointestinal tract in response to the level of the biological condition crossing the predetermined threshold.

2. The capsule of claim 1 wherein the at least one sensor is configured for sensing one or more biological conditions in the gastrointestinal tract; wherein the at least one sensor communicates with the electronic control circuitry for activating the electronic control circuitry to dispense drug according to the drug release profile, or to determine or modify the drug release profile.

3. The capsule of claim 1 wherein the biological condition sensed by the at least one sensor comprises a pH level.

4. The capsule of claim 1 further comprising a wireless communication device for transmitting and/or receiving signals to and from a second communications device located exterior to the body of the mammal; wherein upon receiving a signal from the second communications device, the wireless communication device communicates with the electronic control circuitry device to activate the electronic control circuitry device to dispense drug according to the drug release profile.

5. The capsule of claim 1 wherein the disease is selected from the group consisting of inflammatory bowel disease, celiac disease and intestinal cancer.

6. The capsule of claim 1 wherein the disease is Crohn's Disease or Ulcerative Colitis and the drug is selected from the group consisting of aminosalicylates, corticosteroids, biologics, anti-coagulant drugs, immunomodulators, probiotics and antibiotics.

7. A method for administration of a drug for treatment of a disease in a gastrointestinal tract of a mammal according to a pre-determined drug release profile, the gastrointestinal tract having sites of diseased tissue and normal tissue, the method comprising the acts of:
   orally administering to the mammal an ingestible capsule that includes the drug;
   detecting of a biological condition by at least one sensor included in the capsule, wherein the capsule further includes a drug dispensing device and a controller; and
   in response to the detecting act, activating the drug dispensing device by the controller for dispensing the drug in the gastrointestinal tract according to a predetermined drug release profile, wherein the drug is substantially dispensed at the diseased tissue sites,
   wherein the detecting act includes detecting a level of the biological condition crossing a predetermined threshold, and
   wherein the activating act includes starting a timer for the dispensing of the drug into the gastrointestinal tract in response to the level of the biological condition crossing the predetermined threshold.

8. The method of claim 7 further comprising the act of communicating the sensed biological condition to the controller to dispense the drug according to the drug release profile, or to determine or modify the drug release profile.

9. The method of claim 7 wherein the biological condition sensed by the at least one sensor comprises a pH level.

10. The method of claim 7 further comprising wirelessly communicating signals between the capsule and an external device located exterior to the body of the mammal; wherein the dispensing act is performed in response to a signal from the external device.

11. The method of claim 7 wherein the disease is selected from the group consisting of inflammatory bowel disease, celiac disease and intestinal cancer.

12. The method of claim 7 wherein the disease is Crohn's Disease or Ulcerative Colitis and the drug is selected from the group consisting of aminosalicylates, corticosteroids, biologics, anti-coagulant drugs, immunomodulators, probiotics and antibiotics.

13. The capsule of claim 1, wherein the biological condition sensed by the at least one sensor comprises a pH level, and the at least one sensor is a threshold sensor that detects the pH level crossing the predetermined threshold for starting the timer for the dispensing of the drug into the gastrointestinal tract.

14. The capsule of claim 13, wherein a rate of the dispensing of the drug is proportional to an amount the pH level that differs from the predetermined threshold.

15. The capsule of claim 1, wherein the biological condition sensed by the at least one sensor comprises presence or absence of bacteria or enzymes.

16. The capsule of claim 1, wherein the biological condition sensed by the at least one sensor comprises presence or absence of blood.

17. The method of claim 7, wherein the biological condition sensed by the at least one sensor comprises a pH level, and the at least one sensor is a threshold sensor that detects the pH level crossing the predetermined threshold for starting the timer for the dispensing of the drug into the gastrointestinal tract.

18. The method of claim 17, further comprising the act of varying a rate of the dispensing of the drug in proportion to an amount the pH level that differs from the predetermined threshold.

19. The method of claim 7, wherein the biological condition sensed by the at least one sensor comprises presence or absence of bacteria or enzymes, or presence or absence of blood.

20. The method of claim 7, wherein the capsule further comprises a drug reservoir for storing the drug; and
   a non-digestible outer protective shell housing the drug reservoir, the drug dispensing device and the controller;
   wherein the drug dispensing device is configured to dispense or stop the dispensing of the drug from the drug reservoir into the gastrointestinal tract;
   wherein the controller is configured to communicate with the drug dispensing device for regulating amount and time interval for dispensing of the drug into the gastrointestinal tract by the drug dispensing device according to a predetermined drug release profile,
   wherein the controller comprises a memory for storage or updating of data specific to the predetermined drug release profile for the mammal;
   and wherein the at least one sensor is configured to detect the biological condition and communicate the detected biological condition to the controller for activating the drug dispensing device to dispense the drug in the gastrointestinal tract.

21. The capsule of claim 1, wherein the drug dispensing device includes a valve which is opened by the electronic control circuitry to dispense the drug from the drug reservoir into the gastrointestinal tract, and wherein the electronic control circuitry is configured to open the valve by a fixed amount for a first period of time to dispense the drug at a fixed rate, and to vary opening of the valve during a second period of time to dispense the drug at a variable rate.

22. The method of claim 7, wherein the activating act includes opening a valve of the drug dispensing device by a fixed amount for a first period of time to dispense the drug at a fixed rate, and varying the opening of the valve during a second period of time to dispense the drug at a variable rate.

* * * * *